United States Patent
Goldstein et al.

(10) Patent No.: US 11,298,473 B2
(45) Date of Patent: Apr. 12, 2022

(54) ELECTRONIC VAPORIZER WITH REMOTE CONTROL CAPABILITY

(71) Applicant: Potbotics, Inc., New York, NY (US)

(72) Inventors: Boris Goldstein, New York, NY (US); David Goldstein, New York, NY (US)

(73) Assignee: Potbotics, Inc., New York, NY (US)

( * ) Notice: Subject to any disclaimer, the term of this patent is extended or adjusted under 35 U.S.C. 154(b) by 365 days.

(21) Appl. No.: 15/924,172

(22) Filed: Mar. 16, 2018

(65) Prior Publication Data
US 2018/0263288 A1 Sep. 20, 2018

Related U.S. Application Data

(60) Provisional application No. 62/473,301, filed on Mar. 17, 2017.

(51) Int. Cl.
| | |
|---|---|
| *A24F 13/00* | (2006.01) |
| *A24F 17/00* | (2006.01) |
| *A24F 25/00* | (2006.01) |
| *A61M 11/04* | (2006.01) |
| *G16H 20/10* | (2018.01) |

(Continued)

(52) U.S. Cl.
CPC ......... *A61M 11/042* (2014.02); *A24B 15/167* (2016.11); *A24F 40/42* (2020.01); *A24F 40/485* (2020.01); *A24F 40/53* (2020.01); *A24F 40/60* (2020.01); *A24F 40/65* (2020.01); *A61M 15/0021* (2014.02); *A61M 15/06* (2013.01); *G05B 15/02* (2013.01); *G16H 20/10* (2018.01); *H05B 1/0297* (2013.01); *H05B 3/06* (2013.01); *H05B 3/44* (2013.01); *A24F 40/10* (2020.01); *A24F 40/20* (2020.01); *A61M 15/08* (2013.01); *A61M 2016/0039* (2013.01); *A61M 2205/3334* (2013.01); *A61M 2205/3368* (2013.01); *A61M 2205/3553* (2013.01); *A61M 2205/3584* (2013.01); *A61M 2205/3592* (2013.01); *A61M 2205/3653* (2013.01); *A61M 2205/502* (2013.01); *A61M 2205/583* (2013.01); *A61M 2205/6072* (2013.01); *A61M 2205/8206* (2013.01); *G06K 19/06028* (2013.01); *G06K 19/06037* (2013.01); *G06K 19/0723* (2013.01); *G16H 20/17* (2018.01); *G16H 40/63* (2018.01);

(Continued)

(58) Field of Classification Search
CPC .............................. A24F 40/42; A24F 47/008
USPC ......................................................... 131/329
See application file for complete search history.

(56) References Cited

U.S. PATENT DOCUMENTS

| | | | | |
|---|---|---|---|---|
| 10,334,878 | B2 * | 7/2019 | Leung | A24F 40/51 |
| 2011/0265806 | A1 * | 11/2011 | Alarcon | H02J 7/0047 |
| | | | | 131/273 |

(Continued)

*Primary Examiner* — Abdullah A Riyami
*Assistant Examiner* — Thang H Nguyen
(74) *Attorney, Agent, or Firm* — Khanh T. Glatzel; Premium IP Services, P.C.

(57) ABSTRACT

This invention provides an electronic vaporizer for herbal or medicinal compositions, which may be in solid or liquid form. The cartridge has information on the cartridge content stored in an information storage means such as a unique bar code, QR code, or by NFC means, which is in communication with a remote wireless processor. The electronic vaporizer has an internal computing means to control the system operating parameters and collect usage information, which may be transmitted to other computing means. The vaporizer may be controlled remotely, automatically, or by the user via remote or on-device user interfaces.

16 Claims, 8 Drawing Sheets

(51) Int. Cl.
  *H05B 1/02*     (2006.01)
  *A61M 15/06*    (2006.01)
  *A61M 15/00*    (2006.01)
  *A24B 15/167*   (2020.01)
  *G05B 15/02*    (2006.01)
  *H05B 3/06*     (2006.01)
  *H05B 3/44*     (2006.01)
  *A24F 40/42*    (2020.01)
  *A24F 40/485*   (2020.01)
  *A24F 40/53*    (2020.01)
  *A24F 40/60*    (2020.01)
  *A24F 40/65*    (2020.01)
  *G06K 19/06*    (2006.01)
  *G06K 19/07*    (2006.01)
  *A61M 15/08*    (2006.01)
  *G16H 40/63*    (2018.01)
  *G16H 20/17*    (2018.01)
  *G16H 50/20*    (2018.01)
  *A61M 16/00*    (2006.01)
  *A24F 40/10*    (2020.01)
  *A24F 40/20*    (2020.01)

(52) U.S. Cl.
  CPC ....... *G16H 50/20* (2018.01); *H05B 2203/013* (2013.01); *H05B 2203/021* (2013.01); *H05B 2203/022* (2013.01)

(56) References Cited

U.S. PATENT DOCUMENTS

| | | |
|---|---|---|
| 2013/0340775 A1 | 12/2013 | Juster et al. |
| 2014/0270727 A1* | 9/2014 | Ampolini ............... A24F 40/50 392/387 |
| 2014/0326623 A1 | 11/2014 | Alarcon |
| 2015/0320116 A1* | 11/2015 | Bleloch ............... A61M 11/042 219/628 |
| 2016/0081393 A1* | 3/2016 | Black ..................... A24F 40/65 392/387 |
| 2016/0157524 A1* | 6/2016 | Bowen ................ A61M 11/042 128/200.14 |
| 2016/0219932 A1 | 8/2016 | Glaser |
| 2016/0331027 A1* | 11/2016 | Cameron ............. A61M 15/02 |
| 2017/0014582 A1* | 1/2017 | Skoda .................. A61M 15/06 |
| 2018/0020720 A1* | 1/2018 | Matischek ........... H04B 5/0012 131/329 |
| 2018/0020729 A1* | 1/2018 | Alarcon ................. A24F 40/53 392/404 |
| 2018/0043114 A1* | 2/2018 | Bowen et al. ........ A61M 15/06 131/328 |
| 2018/0177231 A1* | 6/2018 | Woodbine et al. ... A24F 47/008 131/329 |
| 2019/0335817 A1* | 11/2019 | Freeman ........... A61M 15/0065 |
| 2021/0345673 A1* | 11/2021 | Reevell ................... A24D 1/20 |

* cited by examiner

ELECTRONIC VAPORIZER WITH REMOTE CONTROL CAPABILITY

CROSS REFERENCE TO RELATED APPLICATIONS

This application claims the benefit of U.S. Provisional Application No. 62/473,301, filed Mar. 17, 2017. Each of the above-referenced patent applications is incorporated by reference in its entirety.

BACKGROUND OF THE INVENTION

Field of the Invention

This invention relates to an electronic vaporizer with embedded algorithm, wherein the vaporizer facilitates the vaporizing of certain therapeutic materials in liquid or solid form. The vaporizer is electronically controlled and wirelessly connected to remote or cloud computing means. The vaporizer may be controlled by an application on a mobile computing device or a remote computing means and/or a user interface on the vaporizer.

Description of the Related Technology

A vaporizer is a device used to vaporize active ingredients of solid materials or liquid material. Extracted vapor may be collected in an inflatable bag or a hose or pipe before inhalation. Due to the construct of the vaporizers, extracted vapor temperature is lower than the smoking plant materials or liquid materials. A better efficiency in extracting the ingredients may be obtained.

An electronic vaporizer is a battery powered vaporizer, which may simulate the feeling of smoking a cigarette or vaporizing plant materials. Common electronic vaporizers include electronic cigarettes. Activation of electronic vaporizers is commonly by pressing a button. Release rate of active ingredients may not be consistent.

E-cigarettes create aerosol, commonly called vapor, generally containing nicotine, flavors, glycerol and propylene glycol. Its exact composition varies. The main components of an e-cigarette are a mouthpiece, a cartridge (tank), a heating element/atomizer, a microprocessor, a battery, and possibly a Light-Emitting Diode (LED) light on the end. The only exception to this is mechanical e-cigarettes which contain no electronics; the circuit is closed by a mechanical action switch.

SUMMARY

This invention provides an electronic vaporizer with at least one cartridge carrying an information storage means such as a barcode, a Quick Response (QR) code, or a Near Field Communication (NFC) tag containing information on the content. An internal computing processor collects and controls operation parameters while collecting and tracking usage information. Information collected is transmitted to remote computing means for data collection and aggregation. The vaporizer may be controlled by remote applications in communication with the internal computing processor, automatic control protocols embedded within, and/or by users.

In this invention, there is provided a system for vaporizing an herbal composition,
the system comprises:
at least one cartridge configured to house a composition, the cartridge comprising a body, a valve, and a seal, wherein the at least one cartridge carries an information storage means;

an active information retrieving means located at a position suitable for reading, the active information retrieving means configured to retrieve information from the information storage means on the at least one cartridge;
an internal computing processor;
a heating element operatively connected to an internal computing processor and configured to apply heat to the cartridge;
a mouth piece with an opening and a vapor pathway for vapor to pass through from the cartridge seal to the opening;
an air inlet operatively connected to the cartridge;
an airflow sensor operatively connected to the air inlet and configured to measure air volume passing through the air inlet;
a user interface operatively connected to the internal computing processor and configured to display information;
an activation means;
a battery;
a heating chamber wherein the at least one cartridge and the heating element are housed;
a battery chamber wherein a battery is housed; and
a housing element to house the above components,
wherein the heating chamber and the battery chamber are magnetic closed chambers; and
wherein the internal computing processor is configured to collect and process information from the active information retrieving means, the activation means, the airflow sensor, the heating element, and the user interface, to communicate with other computing means within and outside of the system, and to control the system's operation.

There is provided a system as above, wherein the composition is a solid.

There is provided a system as above, wherein the composition is a liquid.

There is provided a system as above, wherein the information storage means is a bar code, a QR code, or an NFC tag containing information and wherein the information contained within the bar code, the QR code, or the NFC tag comprises ingredients of the composition, weight or volume of the composition, dosage, active ingredients and their quantity within the composition, and medical indications for the composition.

There is provided a system as above, wherein the cartridge is designed to maximize internal surface area.

There is provided a system as above, wherein the information collected from the process comprises:
individual session statistics for each use session concerning the heating element temperature, total vapor volume consumed, rate of puffing, time of day when the system is used, the time length of each session, quantity of composition used in each individual session, symptom relief rating input by the user at the user interface;
average statistics throughout the life of the system concerning average heating element temperature, average volume consumed, average rate of puffing during a use session, average time frequency of use per day, average quantity of composition used, and average symptom relief rating input by the user; and
total statistics in the life time of the system concerning total number of vaporization sessions, total usage time, total cartridges used, total quantity of composition used, and total amount of gas volume consumed.

There is provided a system as above, wherein the active information retrieving means is located on a different device than the system.

There is provided a system as above, wherein other computing means that the internal computing processor communicates with are cloud-based processors, virtual machines, desktop computers, laptop computers, and mobile computers.

There is provided a system as above, wherein the other computing means may be accessed and used through a user interface program.

There is provided a system as above, wherein the user interface program is a mobile device application.

There is provided a system as above, wherein the user interface is further configured to receive input information.

There is provided a system as above, wherein the internal computing processor is configured to control the activation means.

There is provided a system as above, wherein the internal computing processor receives information from a remote computing means and use the information to control the activation means.

There is provided a system as above, wherein the internal computing processor is further configured to locate and transmit information concerning the system's location.

There is provided a system as above, further comprising a cooling system to cool the vapor existing the cartridge before it reaches the inhalation opening.

There is provided a system as above, further comprising a LED indicator bar.

In this invention, there is provided a method to control a system for vaporizing a composition, the method comprising:

providing a system as above;

assembling the cartridge into the system operatively compatible with the cartridge;

retrieving information from the information storage means using an active information retrieving means;

activating the cartridge using an activation means;

communicating the information collected from the information storage means to the internal computing processor available inside the system;

using the information collected to adjust heating conditions in the system;

collecting information from the airflow sensor and the heating element and processing the information collected in the internal computing processor; and adjusting operating conditions based on information collected, wherein the information storage means is bar code, the QR code, or the NFC tag.

There is provided a method as above, further comprising the steps of:

configuring the internal computing processor to control the activation means;

comparing information received in the internal computing processor with preset parameters concerning shutting off, the shutting off parameters are stored in the internal computing processor and/or the information storage means provided with the cartridge;

determining whether the shutting off parameters have been reached; and shutting off the system based on information collected.

There is provided a method as above, further comprising the steps of:

providing a remote computing means in operative communication with the internal computing processor;

providing a user interface operatively connected to the remote computing means; and controlling the system by using the user interface, wherein the remote computing means is cloud-based processors, virtual machines, desktop computers, laptop computers, mobile computers, or other computing means capable of receiving, processing, and sending information to and from the internal computing processor.

There is provided a method as above, further comprising the steps of:

configuring the internal computing processor to receive the system's location through the Global Position System;

determining the system location by the internal computing processor;

comparing the system location with a shut off location list, the shut off location list is stored in the internal computing processor or in other remote computing means in operative communication with the internal computing processor;

determining whether the system location is on the shut off location list; and shutting off the system when the system location is on the shut off location list.

ABBREVIATIONS

GPS: Global Positioning System
HIPPA: Health Insurance Portability and Accountability Act
IR: Infrared
LAN: Local Area Network
LED: Light-Emitting Diode
MAN: Metropolitan Area Network
NFC: Near Field Communication
PAN: Personal Area Network
QR: Quick Response
WAN: Wide Area Network

BRIEF DESCRIPTION OF THE DRAWINGS

In the drawings, identical reference numbers identify similar elements or features.

Figure 1:
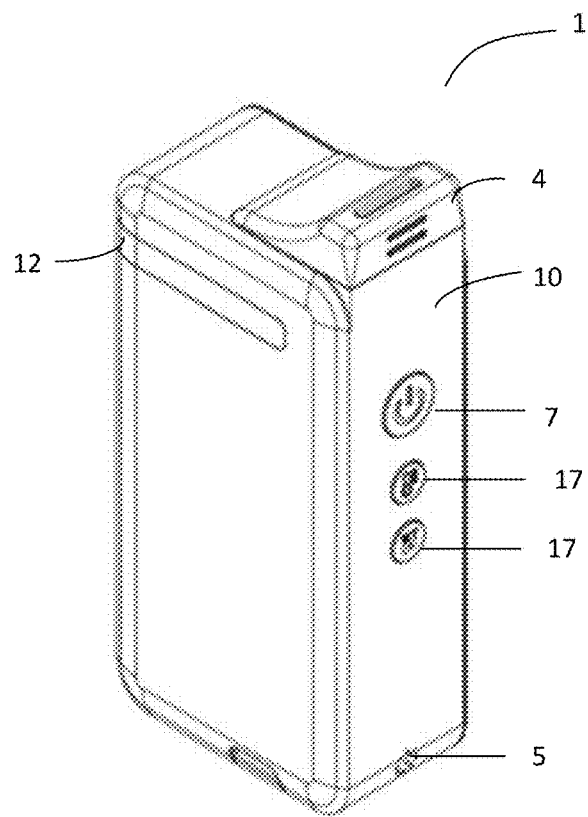
FIG. 1 is the perspective view of the vaporizer fully assembled.

The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements and have been solely selected for ease of recognition in the drawings. Throughout the drawings, identical reference numbers designate similar but not necessarily identical elements.

DETAILED DESCRIPTION OF CERTAIN INVENTIVE EMBODIMENTS

This present invention is capable of being embodied in various forms. The description below of several embodiments is made with the understanding that the present disclosure is to be considered as an exemplification of the claimed subject matter and is not intended to limit the attached claims to the specific embodiments illustrated. The headings used throughout this disclosure are provided for convenience only and are not to be construed to limit the claims in any way. Embodiments illustrated under any heading may be combined with embodiments illustrated under any other heading.

As used herein, the verb "to comprise" in this description, claims, and other conjugations are used in its non-limiting sense to mean those items following the word are included, but items not specifically mentioned are not excluded.

Reference to an element by the indefinite article "a" or "an" does not exclude the possibility that more than one of the elements are present, unless the context clearly requires that there is one and only one of the elements. The indefinite article "a" or "an" thus usually means "at least one." Additionally, the words "a" and "an" when used in the present document in concert with the words "comprising" or "containing" denote "one or more".

Materials used to construct components of the invention herein disclosed may be any materials suitable for the purposes recited herein or other closely related purposes. Any materials referenced herein are for exemplary purpose only and shall not be construed as limiting the embodiments to those materials. The vaporizer according to embodiments herein may be manufactured by conventional manufacturing methods.

Embodiments of this application relate to a vaporizer system controlled by embedded algorithms in communication with remote computing means, which vaporizes liquid or solid materials, which may medicinal materials, contained within at least one prefilled cartridge. The vaporizer may comprise a heating chamber to house the at least one cartridge, liquid or solid medicinal materials to be vaporized may reside inside the at least one cartridge. The at least one cartridge may carry a unique bar code, Quick Response (QR) code, or Near Field Communication (NFC) tag for identification and for setting control parameters. Heating of the cartridge in the heating chamber may be by induction heating, conduction heating, or convection heating. Volumetric airflow through the vaporizer may be measured by an airflow sensor to determine dosage consumed by the user. The vaporizer may be controlled through an algorithm installed on an internal computing processor within the vaporizer. The internal computing processor may collect information concerning usage of the vaporizer and communicate with other computing means to transmit collected data. Computer executable program products on other remote computing means may also control the internal computing processor and thus the system. Users may also control the vaporizer by inputs. The internal computing processor, remote computing means, and the user may control the vaporizer concurrently, in combination with another control means, or separately. The vaporizer may be activated by an activation means and powered by a battery.

Figure 2:
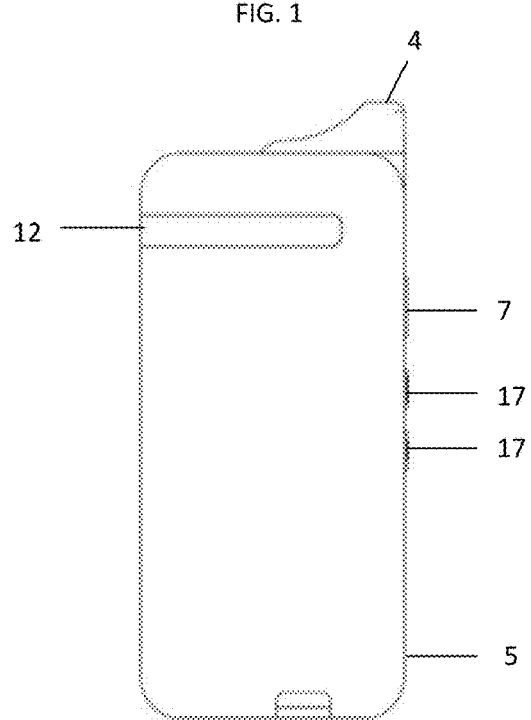
FIG. 2 is the front view of the vaporizer fully assembled.

FIG. 1 is a perspective view of the vaporizer 1 according to an embodiment and FIG. 2 is the front view of the same vaporizer 1. The vaporizer 1 may be in generally rectangular prism shape with a height, a width, and a thickness. The height is the largest length dimension, while the width is the second largest length dimension, and the thickness is the smallest length dimension of a rectangular prism similar to the shape of the vaporizer 1. The front of the vaporizer 1 has a LED indicator bar 12. At the top of the vaporizer 1 is a mouth piece 4 where a user can suck to inhale vapor from the vaporizer 1. On the side wall may an activation means 7, in this case a button, for activation of the vaporizer 1. On the side wall there may also be a user interface 17, which may display temperature and cartridge 2 content level. At the bottom may be an air inlet 5 where air travel through upon inhalation by the user.

Figure 3:
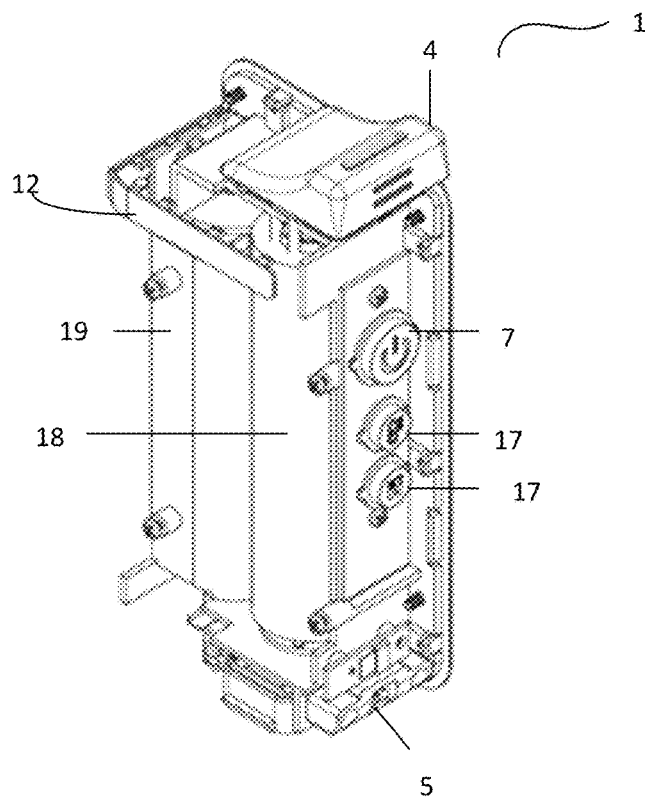
FIG. 3 is the perspective view of the vaporizer showing some internal components without the circuit board.

FIG. 3 illustrates some internal components of the vaporizer 1 according to embodiments. The vaporizer 1 has a heating chamber 18 wherein the cartridge 2 may reside and a battery chamber 19 to house the battery 3. The chambers are magnetic closed chambers, with a magnet on the wall of the chamber and another magnet on the lid of the chamber. The lid can be removed to replace and/or assemble the cartridge 2 or the battery 3 into the respective chamber. At the top of the vaporizer 1 may be a mouthpiece 4 with a vapor pathway 9. At the bottom of the vaporizer 1 may be an air inlet 5 with an airflow sensor 6 located at the air inlet 5 to measure the volume of air travelling through. On the side wall of the vaporizer 1 is an activation means 7, as shown in this embodiment, a button, and user interfaces 17 to display information.

Figure 4:
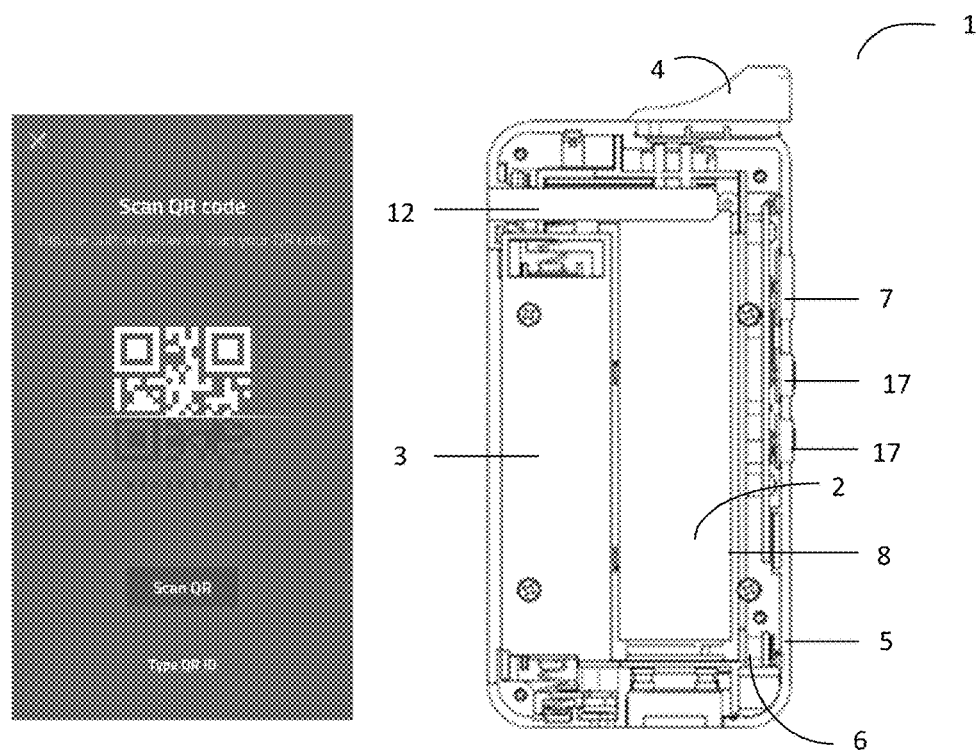
FIG. 4 illustrates the cross section of the vaporizer along the vertical line taken at the middle of the thickness line.

FIG. 4 illustrates a cross sectional view of the vaporizer 1 according to an embodiment taken along the height of the vaporizer 1. The vaporizer 1 has a housing element 10 wherein other components may assembled. The inside of the vaporizer 1 may have a battery chamber 19 and a heating chamber 18, which may house the battery 3 and the cartridge 2 side by side. The heating chamber 18 may have a heating element 8 embedded within, the heating element 8 may surround the cartridge 2 upon assembly. An activation means 7 may be accessed for use on the outside of the housing 10 element. Towards the bottom of the vaporizer 1 may be an air inlet 5 wherein air passes through upon inhalation by the user. The air inlet 5 may have an opening connected to a valve on the heating chamber 19, the air inlet 5 is operatively connected to the cartridge 2. An air flow sensor 6 may be located behind the air inlet 5 to measure air volume passing through during use. Upon assembly, air drawn into the vaporizer 1 by inhalation will travel through the air inlet 5 to the airflow sensor 6 through the valve at the heating chamber 5, then to the cartridge valve 20 into the cartridge 2. A vapor pathway 9 may be present within the mouthpiece 4 to allow vapor to go from the cartridge 2 to the mouthpiece 4 opening where vapor inhalation happens. On the outside of the vaporizer housing 10 may be a LED indicator bar 12 to indicate the vaporizer's 1 status, such as heating or ready to be consumed.

Figure 5:
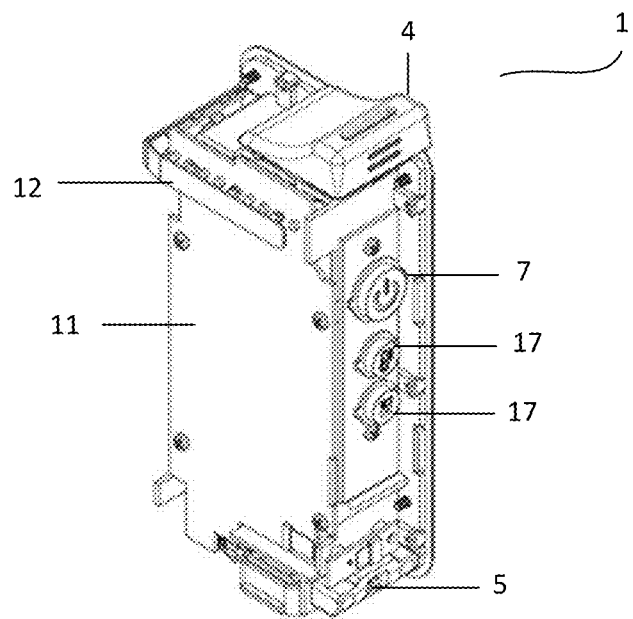
FIG. 5 is the perspective view of the vaporizer showing some internal components with the circuit board.

FIG. 5 illustrates some internal components of the vaporizer 1 according to an embodiment, including a circuit board, which functions as an internal computing processor 11. The circuit board may be of dimensions such that upon assembly the heating chamber 18 and the battery 3 chamber are shielded by the circuit board.

Figure 6:
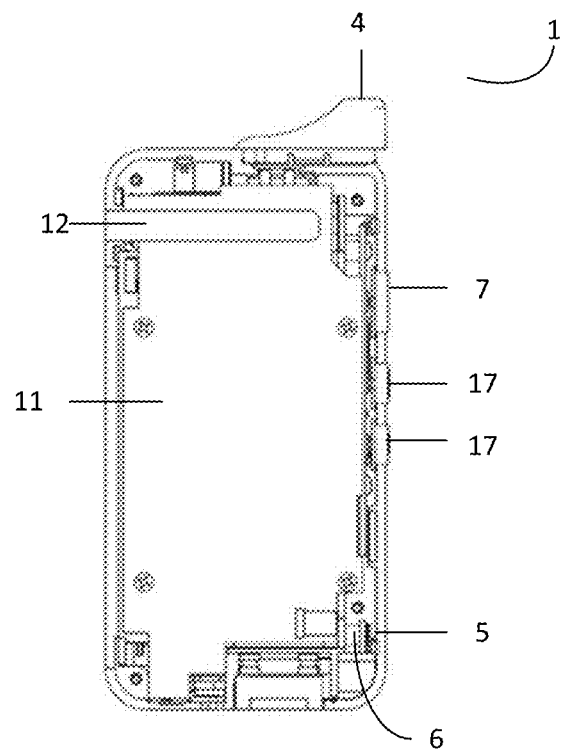
FIG. 6 illustrates the cross section of the vaporizer along the vertical line taken at a position on the thickness line showing the circuit board.

FIG. 6 illustrates front view of the vaporizer 1 shown in FIG. 5. The circuit board lines the interior wall of the housing element 10 such that the circuit board lies between the housing element 10 interior wall and the battery chamber 19—heating chamber 18 area.

Figures 7A, 7B, 7C:
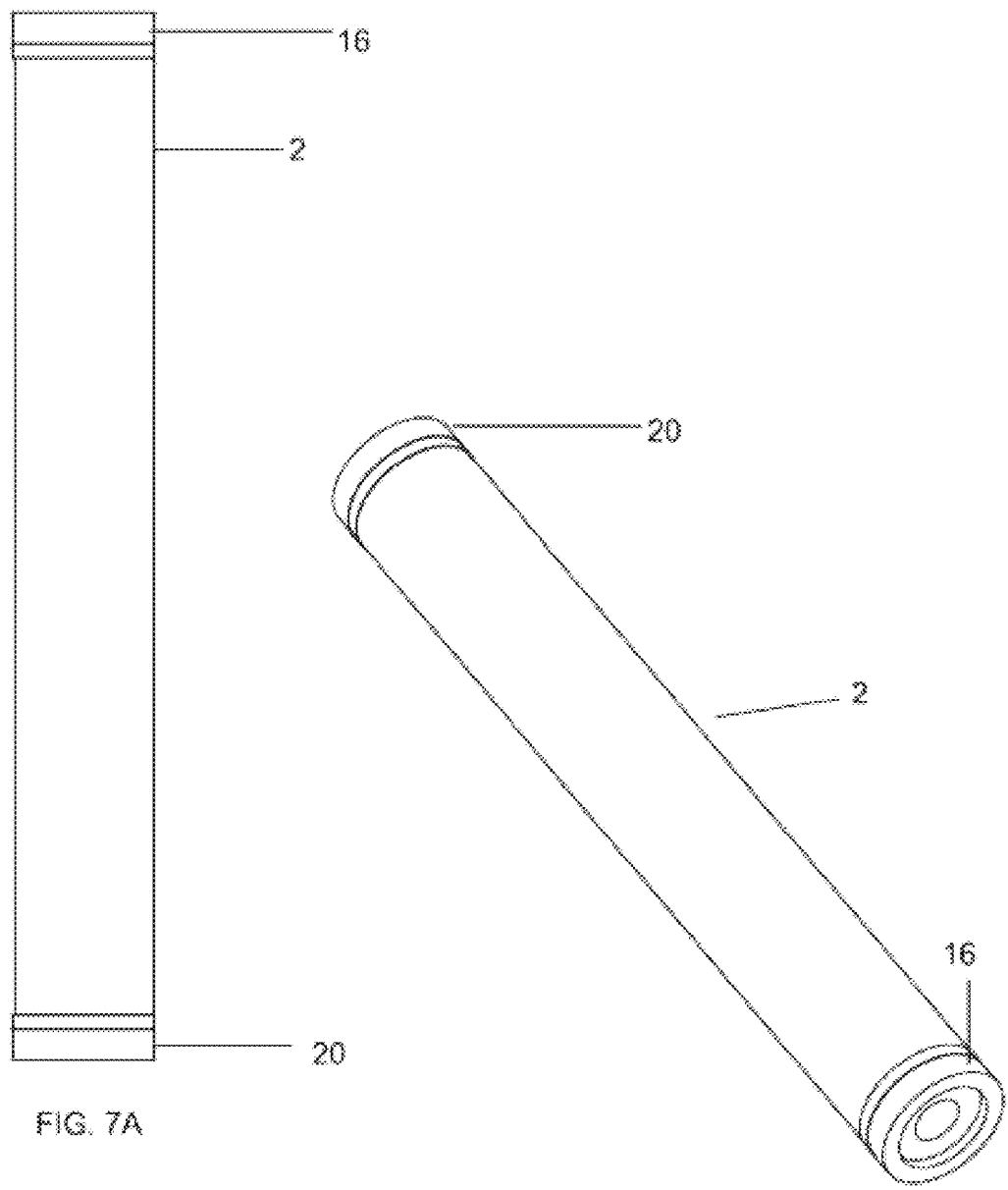
FIG. 7A illustrates the front view of the cartridge.
FIG. 7B illustrates a perspective view of the cartridge.
FIG. 7C illustrates the seal on the cartridge.

FIGS. 7A, 7B, and 7C illustrate the cartridge 2 according to an embodiment. FIG. 7A is the front view of the cartridge 2, FIG. 7B is a perspective view of the cartridge 2, while FIG. 7C illustrates the cartridge seal 16. The cartridge 2 may be in generally cylinder shape to fit with a heating chamber 18 wherein the cartridge 2 may be assembled for heating. A seal 16 may be at one end of the cylinder while a valve 20 may be at the other end of the cartridge 2. Upon assembly, the seal 16 may be operatively connected to the vapor pathway 9 through which vapor generated may travel before reaching the mouthpiece 4. Other shapes allowing heat distribution throughout the cartridge 2 are contemplated.

Figure 8C:
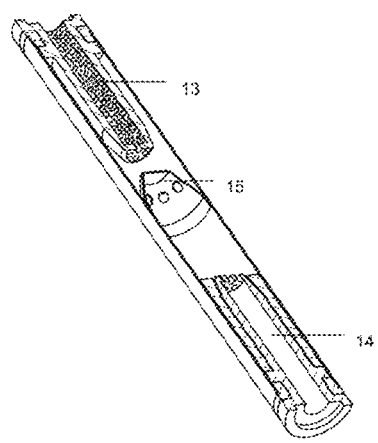
FIG. 8C illustrates the same cross section from a perspective view.
Figure 8B:
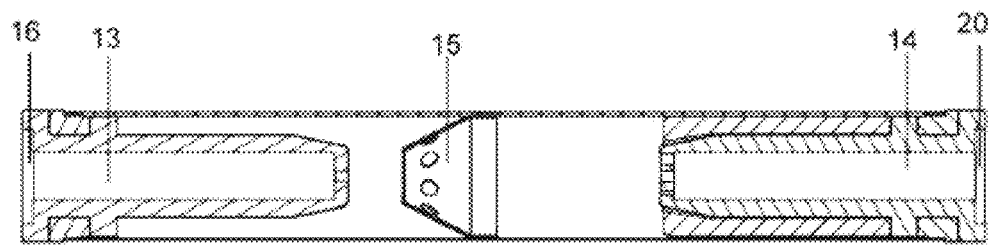
FIG. 8B illustrates the cross-sectional view of the cartridge taken along the length of the cartridge.
Figure 8A:
FIG. 8A illustrates the front view of the cartridge.

FIG. 8A, FIG. 8B, and FIG. 8C illustrate the cartridge 2 and its internal structure of the cartridge 2 according to embodiments. A cylinder cartridge 2 may have a material chamber 13 separated from a drip chamber 14 by a concentrate dish 15. The material chamber 13 may contain the material to be vaporized. When the user sucks on the mouthpiece 4 to inhale, air may go through the air inlet 5 into the cartridge 2 at the cartridge valve 20. Upon heat application, heated materials may generate vapor, which may travel through the concentrate dish 15 into the drip chamber 14 prior to existing the cartridge 2 through the seal 16.

Figure 9:
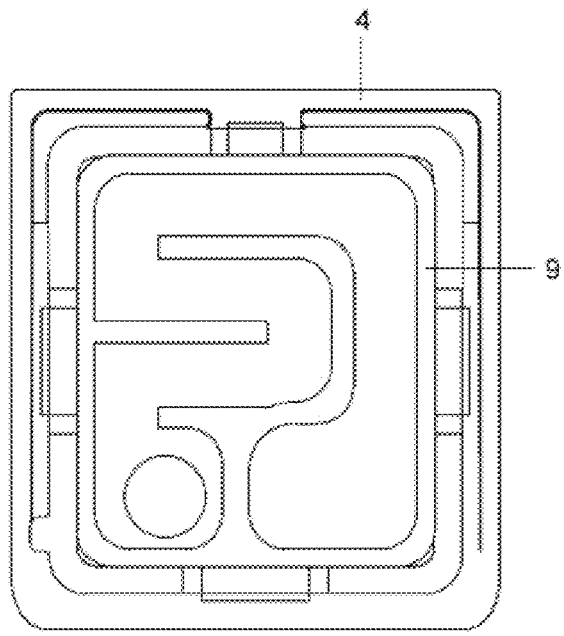
FIG. 9 illustrates the bottom view of the mouthpiece.
Figure 10:
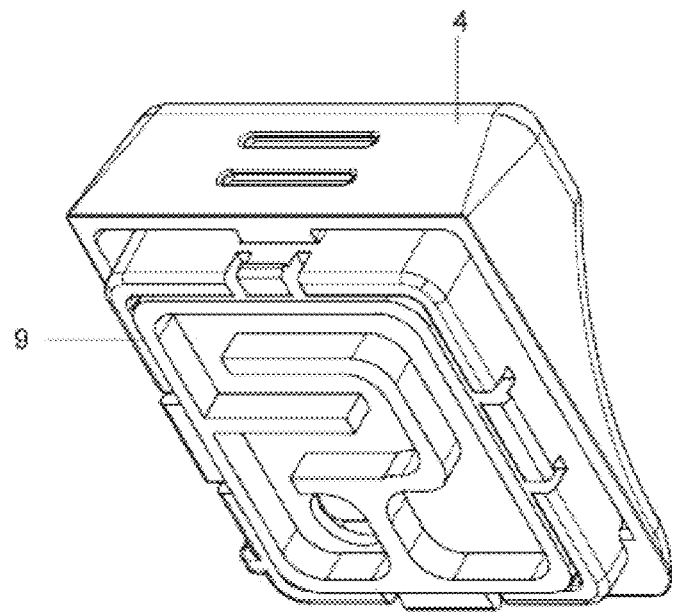
FIG. 10 illustrates a perspective view of the mouthpiece.

FIG. 9 illustrates the mouthpiece 4 bottom view showing a vapor pathway 9 while FIG. 10 illustrates a perspective view of the same mouthpiece 4. The mouthpiece 4 may be located on the vaporizer 1 at a location that is suitable for connection to the cartridge's seal 16, such that vapor produced by heating and pulled out of the cartridge 2 by inhalation may travel to the vapor pathway 9. The vapor pathway 9 may end at the mouthpiece 9 opening, where vapor may escape the vaporizer 1 and be inhaled by the user.

The arrangement of the components described above is by way of example only. Other arrangements are contemplated. The shape of the vaporizer 1 and other components within may also vary, and the drawings included herein are illustrations of an embodiment only. These descriptions shall not be construed to limit the vaporizer 1 according to embodiments hereby to be limited to the size, shape, or arrangement described.

In embodiments, the cartridge 2 may be designed to store up to 3 grams of dry herbs or solid or 2 grams of liquid in the nature of herbal extract or medicinal liquid. In another embodiment, the cartridge 2 may store 0.5-2 grams of dry herb or 0.5-2 grams of liquid. Other capacities are contemplated. Dry herbs or liquid may be burnt and/or vaporized by heat application to the cartridge 2 to release active ingredients contained therein.

The cartridge 2 may be made with SAE 304 SS stainless steel (A2 stainless steel), alumina oxide ceramic ($Al_2O_3$), peek high temperature plastic, titanium, graphene, borosilicate glass, or other materials suitable for this purpose. The cartridge 2 valve may be made from silicon. The material used to make cartridge 2 may be capable of heat conduction while maintaining structural integrity during heating cycles and long-term exposure to heat. Preferably materials used to make the cartridge 2 do not contain other materials that may be leached into the content of the cartridge 2.

In embodiments, active ingredients may be provided in various forms, including solid or liquid with variable viscosity, or paste. The active ingredients may be provided as natural herbal extract. Active ingredients from other sources and in other forms are contemplated.

The liquid provided in the cartridge 2 may contain active ingredients mixed with other liquids suitable for vaporizing, including but not limited to propylene glycol, glycerin, water, certain flavors, among other suitable ingredients. Active ingredients may need to be provided in small dosage, such as 100-500 mg of total active ingredients in each prefilled cartridge, thus other liquid materials may be needed to provide a quantity sufficient for vaporizing. Higher dosage may also be provided, however bulking materials may or may not be needed. Active ingredient may also be provided without other added materials. More than one active ingredient may be included.

Flavors added into the liquid for vaporization may include banana, peach, strawberry, blueberry, coconut, raspberry, dragon fruit, apple, peach, honey dew, mango, pineapple, pomegranate, kiwi, lemon, watermelon, cherry, orange, grape, cotton candy, butterscotch, candy cane, caramel, peppermint, spearmint, tart, cookie, custard, banana bread, peanut butter, vanilla, or menthol. A combination of flavors or other flavors may be added.

The content of the cartridge 2 may be provided in solid form. Dry herbs may be dried using conventional techniques and may be infused with other ingredients to change the aroma and/or add other active ingredients as needed. Solid herbal form of active ingredients may also be filled into the cartridge 2 for heating in the same manner as a liquid cartridge 2. Solid herbal cartridges may be used in vaporizers according to embodiments, even though dosage control for herbal cartridges may be less accurate. Other medicinal solids may be used in the cartridges.

In embodiments, active ingredients provided in liquid form, such as oil extracted from herbal sources, may be pre-mixed with the exact composition. This may provide control over the types of active ingredients, other ingredients, sources, and ratios of ingredients. These parameters may be determined by an Artificial Intelligence program. Upon determination of active ingredient content, a prescribing physician may prescribe a specific type of cartridge 2 with exact ingredients. By providing pre-filled cartridges, the user may control the exact amounts of active ingredient to be used, while the prescribing physician may be able to order the precise amount.

An automatic filling line may be used to fill both solid herbal and liquid cartridges. Automatic filling may improve precise ingredient specification and consistency among various cartridges of the same kind. Each cartridge 2 may comprise a valve for air inlet upon vaporizing. Each cartridge 2, upon filling, may be capped and sealed prior to packaging.

In embodiments, the cartridge 2 may comprise a body in generally cylindrical shape, while other shapes and configurations are contemplated. The prefilled cartridge 2 may be sealed with a seal 16 on one end and may have a valve 20 on the other end. A sealed environment in the cartridge 2 may prevent leakage, which in turn may increase efficiency and improve the vaporizer's operation overall. A valve may also be configured to lock and stop vapor discharged from the cartridge 2 when a pre-set inhaled amount has been reached. The cartridge's valve may be at the bottom, such that the valve is operatively connected to the air inlet 5 upon assembly into the cartridge 2.

Cartridge 2 configured to operate in this manner may provide a means to control dosages in each cartridge 2. Dosage may further be controlled by additional mechanisms to measure consumed amounts. The prescribing physician therefore may control the dosage used by prescribing the appropriate cartridge 2 and/or duration of consumption. The physician may additionally adjust the dosage by initiating control measures through a computer executable program product installed on a separate and remote computing means in communication with an internal computing processor 11 within the vaporizer 1. The internal computing processor 11 may be a circuit board.

In embodiments, each prefilled cartridge 2 may be provided with an information storage means such as a unique barcode, QR code, or NFC tag upon which information about the cartridge's content may be stored. The information storage means may be on the cartridge's 2 wall or included into the cartridge's 2 packaging. Upon insertion into the vaporizer 1, the cartridge's 2 unique information may be registered, enabling collection of information during cartridge 2 usage. The information contained may also be used to determine and adjust vaporizer 1 settings to fit with the specific cartridge 2. Alternatively, the cartridge 2 may carry NFC-enabled communication means to communicate stored information within the cartridge 2.

In embodiments, information contained in the bar code, QR code, or within the NFC tag or other information storage means may comprise ingredients of the composition to be vaporized present inside the cartridge 2, weight or volume of the composition, dosage, active ingredients and their quantity within the composition, and medical indications for the composition, among other information. The composition may be herbal composition or other types of composition.

In embodiments, the vaporizer 1 may comprise an active information retrieving means located at a suitable position to retrieve information from the information storage means, such as by scanning the bar code, QR code, or NFC tag on the at least one cartridge 2. The active information retrieving means may also be locate at a remote computing means such as a mobile application. Other remote computing means used as an active information retrieving means are contemplated. Upon scanning, the active information retrieving means may collect information provided by the bar code, QR code, or NFC tag and transmit the collected information to the internal computing processor 11 for use in the control of the vaporizer 1. Working conditions for the vaporizer 1 may also be adjusted upon collection of this information.

In embodiments, a battery 3 may be provided to power the vaporizer 1, such that the heating element 8 may generate heat and the internal computing processor 11 may operate to collect and transmit information and control the vaporizer 1. The battery 3 may be housed in the battery chamber 19 and operatively connected to the heating element 8, the circuit board (or the internal computing processor) 11, and optional a user interface 17 and/or LED indicator bar 12 to power the vaporizer 1. The battery 3 may be operatively connected to other components to provide necessary power for operation of the vaporizer 1.

In embodiments, a heating element 8 may be provided in contact with the cartridge 2 upon assembly into the vaporizer 1. The heating element 8 may line the inside surface of the heating chamber 18, such that the heating element 8 can conduct heat to the cartridge 2. The heating element 8 may also be in operative contact with the cartridge 2 at different locations and in different manners. When heated, liquid or herb inside the cartridge 2 may vaporize or burn and produce vapor. Upon vapor generation by the heating mechanism, the user can suck on the mouthpiece 4, creating a suction and thereby moving the vapor through the vapor pathway 9 to the mouthpiece 4.

In embodiments, the cartridge 2 may be designed to maximize internal surface area to increase heat absorption by the material within the cartridge 2. The heating element 8 may be designed to provide even heating on the entire cartridge's 2 heat conduction surface, such that solid or liquid material inside the cartridge 2 at different locations receives substantially the same amount of heat throughout the heating period.

In embodiments, the heating element 8 may operate in heating cycles, wherein heat is generated and transferred through the mass, in this case the cartridge 2, its components and content. Upon reaching a desired temperature and distribution, the mass may be cooled down before another heating cycle may start. Heat control may generate the same amount of vapor from the content in each heating cycle and therefore control the dosage generated. Heating tolerance is ±5° C., which is the difference between the pre-set temperature and actual temperature as measured.

Heating of the cartridge 2 content may be by induction heating, wherein a metal core such as high temperature steel is heated by electromagnetic induction. The heating core may be located at the bottom or along the cylindrical wall of the cartridge 2 and heat is distributed throughout the cartridge 2 by the heating mechanism. Heat generated in the metal core by eddy currents flows through the metal core, which in turn heats the liquid or solid content in the cartridge 2. Heated liquid or dry herbs solid may vaporize and vapor may exit the cartridge 2 through the cartridge seal 16.

Heating of the cartridge 2 content may be by conduction heating, wherein a cylindrical heating chamber 18 transfers heat to the cartridge 2 locate within. A heating film comprised of polyimide electrothermal film capable of being set to specific temperatures is located along the cylindrical surface area of the heating chamber 18, which in turn heats the liquid or dry herb content in the cartridge 2. Heated liquid or dry herbs may vaporize and vapor may exit the cartridge 2 through a valve. Other materials for heating film are contemplated.

Heating of the cartridge 2 content may be by convection heating, wherein in an oven located at the bottom of the heating chamber 18 is set to a specific temperature, applying indirect heat to the cartridge 2 within the chamber above the oven. When a subject inhale from the vaporizer's mouthpiece 4, hot air transfers upward from the oven to the cartridge 2, which in turn heats the liquid or dry herbs content in the cartridge 2. Heated liquid or dry herbs may vaporize and vapor may exit the cartridge 2 through the cartridge seal 16.

After each heating cycle, once the vapor has passed through the seal 16, the cartridge 2 may cool down by reducing heat at the heating element 8 and/or by a cooling mechanism. Vapor generation may terminate after vapor exiting the valve, thereby limiting vapor volume exiting through the valve. Vapor may then travel from the valve through the vapor pathway 9 before reaching the mouth piece 4 opening.

In embodiments, vapor coming out of the cartridge 2 may pass through a vapor pathway 9 before reaching the inhalation opening on the mouthpiece 4. The vapor pathway 9 may be made of silicon or other suitable materials, such that heat absorption may happen as vapor travels along the vapor pathway 9. In the mouthpiece 4 according to embodiments, the vapor pathway 9 may be a maze-like pathway, such that heat conduction area is maximized. Cooling mechanisms may be present on the vapor pathway 9 or the vapor may cool down by contact between the hot vapor and the vapor pathway 9. An extended pathway between the mouth piece 4 and the cartridge seal 16 where vapor travels through prior to exiting the vaporizer 1 may provide extra cooling. The length of vapor pathway 9 may be modified for cooling effect.

In embodiments, volumetric airflow of air coming into the at least one cartridge 2 may be monitored and controlled by volumetric airflow sensor 6. The airflow sensor 6 may measure the volume in milliliters of air pulled into the cartridge 2. The airflow sensor 6 may be located at the entrance before cartridge valve 20, right after the air inlet 5. Air drawn into the cartridge 2 at the air inlet 5 may be measured by the airflow sensor 6 after passing through the air inlet 5.

The airflow sensor 6 may be a pressure sensor. When the vaporizer 1 is activated by the activation means 7, the airflow sensor 6 may measure the volume of air drawn into vaporizer 1 due to inhalation. The airflow sensor 6 may be incorporated into the vaporizer 1 at the air inlet.

In embodiments, an internal computing processor 11, which may be present as a circuit board, may collect statistics information from individual sessions concerning the heating element 8 temperature, total air volume consumed, rate of puffing, time of day when the system is used, the time length of each session, quantity of composition used in each individual session, or symptom relief rating input by the user. The internal computing processor 11 may collect average statistics information throughout the life of the system concerning average heating element 8 temperature, average volume consumed, average rate of puffing during a use session, average time frequency of use per day, and average symptom relief rating input by the user. The internal computing processor 11 may also collect total statistics information in the life time of the vaporizer 7 concerning total number of vaporization sessions, total usage time, total cartridges used, total quantity of composition used, and total amount of air volume consumed. Information collected may be from the airflow sensor 6, cartridge valve 20, heating element 8, cartridge seal 20, or other components of the vaporizer 1.

Information collected from the volumetric airflow sensor 6 may be processed by a built-in internal computing processor 11. The internal computing processor 11 within the system may alert the user that the prescribed dosage has been reached and the user may stop further inhalation. Alert may be by ways of sound alert, light blinking alert, a message displayed on a user interface 17, or other methods. Alternatively, the internal computing processor 11 may process information received from the volumetric airflow sensor 6 before sending such information to a mobile application and/or a remote computing processor such that appropriate actions may be initiated. Cloud computing control of the vaporizer 1 may be by communication between the vaporizer's 1 internal computing processor 11 and the mobile application or remote computing processor through the cloud.

Once the prescribed dosage has been reached, the vaporizer 1 may alert the user to stop, which may prevent an overdose. While adverse events relating to overdose of active ingredients may or may not be apparent, control of dosage may be necessary to provide optimum therapy conditions. Real time control of the dosage and dosage tracking may be carried out by this volumetric airflow control and communication of information collected to the computing means via cloud computing.

In embodiments, a shut off mechanism may be provided within the system. When a preset parameter, such as temperature or air inlet volume in a session has been reached, or system location is on a shut off list, the internal computing processor 11 may send a signal to the activation means 7 to shut off the vaporizer 1. Shut off may also happen remotely via cloud computing, such that the shut off signal is sent from a remote computing processor to the internal computing processor 11 to connect with the activation means 7 to shut off the vaporizer 1.

In embodiments, a cooling system may be optionally provided. Upon exiting the heating compartment through the seal 16, hot vapor may pass through an outflow cooling system, which may be a cooling system designed to reduced vapor temperature. In the cooling system, hot vapor temperature may be reduced to an appropriate temperature suitable for the user's inhalation. Control may be by the user interface 17 on the vaporizer 1 or by a remote executable computing program product, including, but not limited to, a mobile device application. Temperature sensor within the cooling chamber may send a signal upon which cooled vapor may be discharged from the cooling chamber. By cooling down the vapor, the user may not cough or vomit during use.

In embodiments, once the cartridge 2 is empty, a signal may be sent to alert the user Notifications of near-empty cartridges, such as at 80% or 60%, or any other percentages as necessary, may be sent to users and displayed on a remote user interface, such as a mobile application. Replacement of empty cartridges and preparation for new cartridges may be initiated upon receipt of appropriate signals.

Cartridge 2 content in volume during use may be calculated by an algorithm embedded in the internal computing processor 11 or in a remote computing means, such as a designated mobile application, and displayed in the user interface 17 on the vaporizer 1 or a user interface on a remote computing means. Information concerning the materials contained inside a cartridge 2 and information from the airflow sensor 6 may be used in this algorithm. For example, a cartridge 2 with certain materials may be estimated to be able to generate X volume of vapor. After a certain amount of air has been drawn into the vaporizer 1 during use at a certain temperature, it can be calculated that a certain amount vapor has been generated and a certain amount of material has been burnt. Therefore, the cartridge 2 content left over can be estimated.

Embodiments of this invention provide a vaporizer 1 with precise control means, wherein precise active ingredients may be provided, and dosage consumption may also be controlled. Consumption of active ingredients via inhalation may not be easily controlled for precise dosages. The vaporizer 1 according to embodiments may overcome this difficulty.

In embodiments, the vaporizer 1 may comprise a user interface 17 on the vaporizer, such that certain parameters may be controlled in operation of the vaporizer 1 and certain information may be displayed. The user interface 17 may also be used to switch the vaporizer 1 on/off and control which information may be collected or transmitted by the internal computing processor 11.

In embodiments, device settings and control panel for the vaporizer 1 may be controlled remotely by a designated mobile application or other user interfaces on other remote computing means. The designated mobile application may be operable on other devices, including mobile computer devices, such as mobile phones, tablets, or laptop computers, and desktop computers or other non-mobile computing means. The mobile application may enable continuous upgrade of the firmware, wherein the firmware may be pushed back to the vaporizer 1. An upgrade to a mobile application or a user interface in a remote computing means may also upgrade the internal computer. The designated mobile application may also enable users to easily control the vaporizer 1 from their mobile devices.

Additionally, the vaporizer 1 may be controlled by a separate computing program product executable on a remote computing means, such as a software in a remote computer. Remote computing means may be a desktop computer, a laptop computer, a mobile computer, or a virtual machine computer, among other computing means. Vaporizer control may be effectuated from these computing means.

On the other hand, information collected by the vaporizer's 1 internal computing processor 11 may be used by the vaporizer 1 to adjust heating and working settings to fit the specific cartridge 2. Heating and working settings may in turn determine the amount of active ingredients released during use.

In embodiments, information collected from the above components embedded in the vaporizer 1 by the internal computing processor 11 may be transferred via a wired connection or a wireless connection, such as a Bluetooth connection, to other computing means. Other wireless network connections via personal area network (PAN), local area network (LAN), metropolitan area network (MAN), or wide area network (WAN) may be utilized in wireless communication between the internal computing processor 11 and other computing means. Other connection means between the vaporizer's internal computing processor 11 and other computing means are contemplated. Information transferred may be sent directly to a cloud system for tracking, registering, monitoring, and analyzing of information. The cloud system may directly control the vaporizer 1 for operation according to the settings. The vaporizer 1 may be turned on and off by remote control of an activation means 7. Alternatively, the vaporizer 1 may be turned on and off remotely via an on-off electronic switch, which may be wirelessly controlled. The ability to turn the vaporizer 1 on and off remotely may be useful in preventing overdose wherein the off signal is generated upon alert of over-consumption, preventing usage at inappropriate locations, and child-proofing.

In embodiments, components of the vaporizer 1 disclosed herein and other ancillary components necessary for operation of a vaporizer 1 as known in the art are housed in a housing element 10. The housing element 10 may provide the support structure for components of the vaporizer 1 and protect the components inside. The housing element 10 may be made of metal frames such as stainless steel, heat-enduring plastic, or silicon, or other materials suitable for the purpose.

Figure 11:
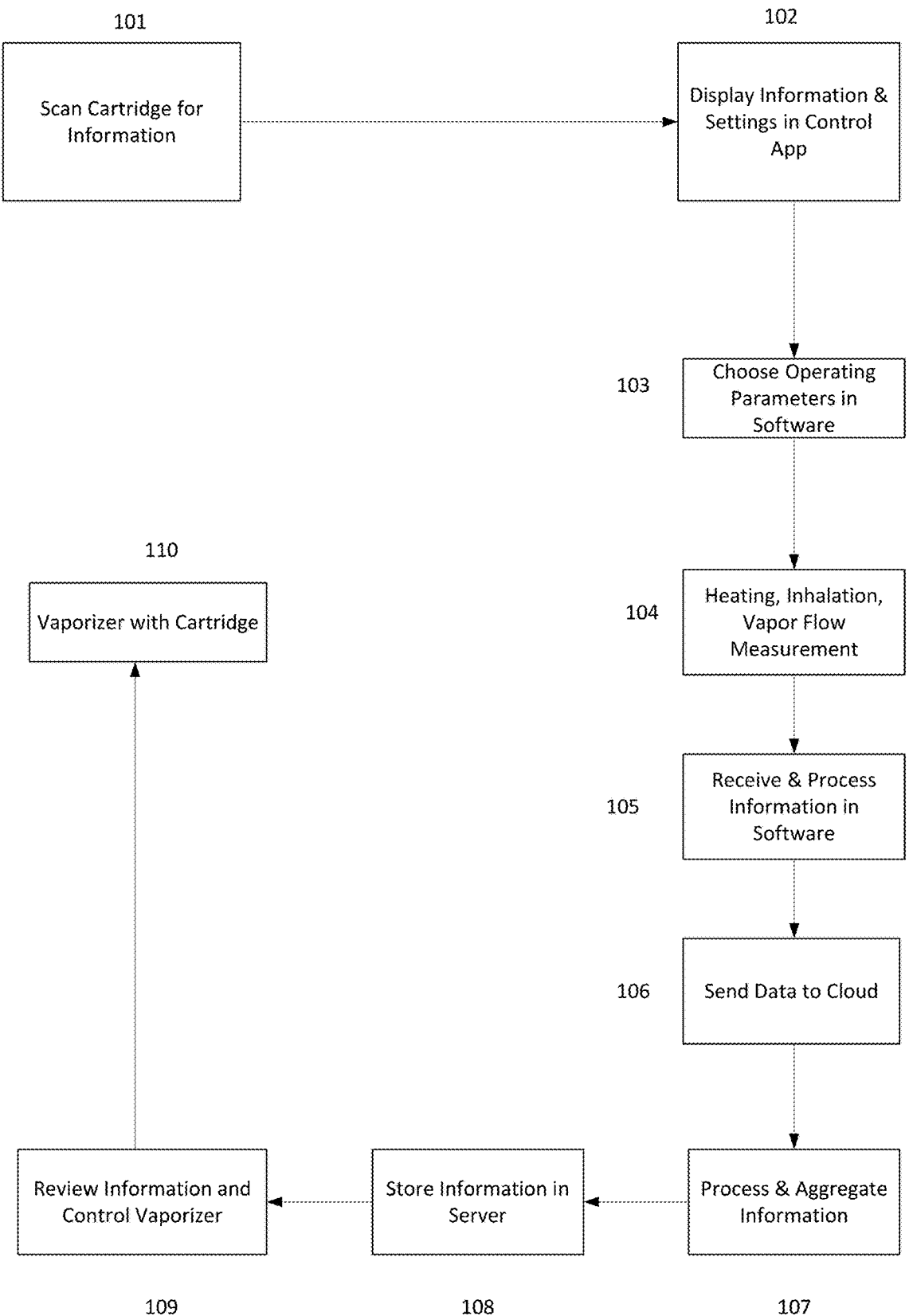
FIG. 11 is the algorithm steps showing the operation of the vaporizer and interaction between the vaporizer and remote computing means.

In use of the invention, at least one cartridge 2 according to embodiments may be assembled to the vaporizer 1, the vaporizer 1 is operatively compatible with the cartridge 2 and capable of using the cartridge 2. FIG. 11 illustrates working steps of the vaporizer 1 in these embodiments. At step 101, the active information retrieving means may scan the at least one cartridge 2 to collect information contained in the information storage means, such as the bar code, QR code, or NFC tag. Retrieving information from the information storage means, such as by scanning of the barcode or the QR code or receiving information from NFC tag may be by a wireless device with computing means to receive information stored on the cartridge 2 or cartridge 2 packaging. The active information retrieving means may also be built into the vaporizer 1. The information retrieved may be transmitted to the internal computing processor 11, upon which the vaporizer's 1 working conditions may be adjusted.

At step 102, information retrieved from the bar code, QR code, or NFC tag may be displayed on a user interface 17, which may be built in on the vaporizer 1 or available on a remote computing means as a mobile application or an executable computing program product. At step 103, on this user interface available on the remote computing means, operating parameters may be chosen or recommended, which are then communicated to the internal computing processor 11 for implementation. Automatic options to operate the vaporizer 1 based on the cartridge's 2 information may also be displayed and chosen.

The ability to adjust working conditions according to the cartridge's 2 identification may enable manufacturers to manufacture different cartridges with different materials and/or material combinations without affecting dosage or active ingredient quantity discharge. Moreover, automatic setting adjustment may relieve users of the burden of setting working conditions to fit with the cartridge 2 use and/or dosage or use requirements. Each cartridge 2 may be tracked for usage and consumption, and an alert may be sent when cartridges are empty. Setting control may also ensure consistent release of active ingredient amounts and maximum efficiency by controlling temperature and dosing for each cartridge 2 material.

Once the vaporizer 1 is activated for use, the heating element 8 may heat the cartridge 2 to vaporize the content. The information collected from the bar code, QR code, or NFC tag may be used by the internal computing processor 11 to adjust the heating temperature. Other settings, such as discharged temperature, may also be controlled to fit with the user's need.

At step 104, the vaporizer 1 works by heating the cartridge 2 and discharging vapor. Other components of the vaporizer 1 may measure and collect information. The airflow sensor 6 may measure the air volume passing through to the cartridge 2. Once the desired temperature, such as the preset temperature according to the cartridge's 2 information or the temperature set by the user, has been reached, the user may inhale by sucking on the mouthpiece 4, causing the vapor to flow along the vapor pathway 9. A cooling system may be available and cool the vapor down before it reaches the inhalation opening. Alternatively, vapor temperature may reduce after travelling through a vapor pathway 9 within a mouthpiece 4 prior to reaching the mouthpiece 4 opening.

At step 105, the internal computing processor 11 may collect information relating to individual sessions, average values across sessions, and total statistics information as above. At step 106, this information may be transmitted to remote computing means for collection, adjustment, or control of the vaporizer 1. At step 107, the remote computing means, which may be a cloud computing means, aggregates and processes information. At step 108, information collected from the vaporizer's internal computing processor 11 may be stored and may be retrieved therefrom for other purposes, including research and public health data storage.

Information collected may be used by the internal computing processor 11 to continuously adjust working parameters to effectively control the vaporizer 1. Heating temperature and cooling temperature may be adjusted along with other parameters as the user inhales. The internal computing processor 11 may also "self-learn" and use information stored to adjust the system to work better in later use.

At step 109, information from the vaporizer 1 may be displayed and reviewed, from which control of the vaporizer 1 may be conducted by the user via a user interface 17, which may be on the vaporizer 1 or available on a remote computing means, such as an application in a mobile computing device. In embodiments, information collected from the vaporizer 1 may optionally be available to prescribing physicians via a computing means with remote control. The prescribing physician therefore may monitor usage and adjust settings to increase/reduce dosage at any time. Particular and identifiable cartridge 2 usage may enable identification of patient's identity, such that the prescribing physician may adjust control settings according to the patient's evolving need.

When the consumption on a cartridge 2 is recorded to have reached a certain point, the vaporizer 1 may shut itself off to prevent overdose. This information may be calculated by the internal computing processor 11 from the airflow measured by the airflow sensor 6. Remote computing means may also be used to shut off the vaporizer 1 upon an alert of a possible overdose. Internal control settings may also shut off the vaporizer 1.

In embodiments, the internal computing processor 11 may also be configured to receive information concerning the vaporizer's 1 location via the Global Positioning System (GPS), such that location information may also be collected for monitoring the usage location, such as which state the device is used in. This location information may be compared to a list to determine if the device is within an area where it is legal to be used or not. This is particularly important when the vaporizer 1 is used to vaporize cannabis products. Where appropriate, the off switch may be activated automatically or by the prescribing physician's decision if GPS location indicates that the vaporizer 1 may be located outside a state wherein medical cannabis is legal. Other unique or custom settings may be available per the user's need.

Various control functions available in this vaporizer 1 may be set such that the user may have control of certain functions while the prescribing physician may have control of other functions. Functions available to the user and the prescribing physician may overlap or exclusive from each other.

Figure 12:
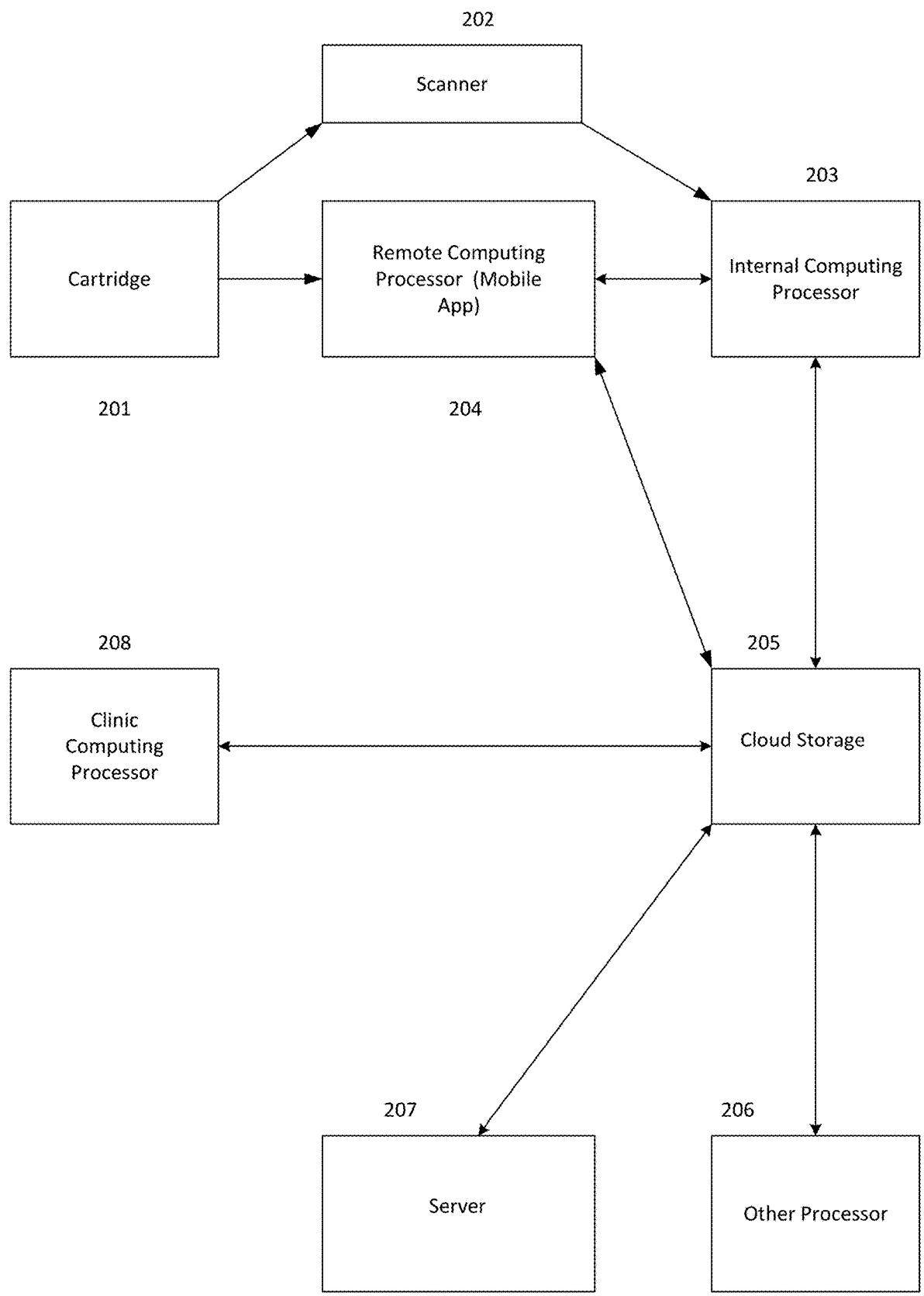
FIG. 12 is the data flow in the interaction between the vaporizer and the remote computing means.

FIG. 12 illustrates the data flow between the vaporizer, the cartridge, the internal computing processor, the cloud storage, remote processors, and server. Each data processing and/or storage point interacts with other data processing and/or storage points, such that information is exchanged, aggregated, and learnt, the results of which may control or contribute to the control of the vaporizers in embodiments. Information collected and processed may also be used by other processors and/or other users for purposes.

In embodiments, information collected by the internal computing processor 11 may be collected and aggregated in compliance with the Health Insurance Portability and Accountability Act (HIPPA) and uploaded to the cloud or other computing means to contribute to the knowledge database concerning herbal consumption. This information may be used in collaboration with other information uploaded by other devices.

In FIG. 12, the cartridge information storage means 201 is the first source of data, which is stored in the information storage means, such as the bar code, QR code, or NFC tag, such data may concern the content of the cartridge and other parameters related to the use of the cartridge. Data from the cartridge 201 may flow to the active information retrieving means 202, such as a scanner, and therefrom may be used to control and operate the vaporizer.

Data from the active information retrieving means 202 may flow to the internal computing processor 203, which may control the operation of the vaporizer. Data from the active information retrieving means 202 may also flow to a remote computing means 204, such as a mobile application. Data flow between the internal computing processor 203 and the remote computing means 204 may be in two directions, such as each side receives information from the other side.

Data from the internal computing processor 203 may flow to a cloud storage 205 through the remote computing processor 204. Data from the internal computing processor 203 may include data concerning the operation of the vaporizer. In the reverse direction, the cloud storage 205 may aggregate data and/or feed data back to the remote computing means 204 and the internal computing processor 203. For example, if a QR code of a certain kind of cartridge is associated with a temperature, this information can be fed back into the internal computing processor 11 from the cloud storage, such that the device "learns" a better operating parameter.

Data from the cloud storage 205 may flow to other processors 206, wherein data is further processed and may flow back to the cloud storage 205. Data from the cloud storage 205 may also flow to clinic computing processors 208 for review and decision making. Finally, data from the cloud storage may flow to a server 207, which may store, aggregate, and process data.

Data may flow from the clinic processors 208, other processors 206, and the server 207 back to the cloud storage 205 then to the remote computing means 204 and eventually to the internal computing processor 203. This data flow may allow information to be communicated between various processing points through the cloud storage 205, thereby enabling remote control, information collection, and self-learning for the vaporizer.

Variations and modifications will occur to those of skilled in the art after reviewing this disclosure. The disclosed features may be implemented, in any combination and sub-combination (including multiple dependent combinations and sub-combinations), with one or more other features described herein. The various features described or illustrated above, including any components thereof, may be combined or integrated in other systems. Moreover, certain features may be omitted or not implements.

Examples of changes, substitutions, and alterations are ascertainable by one skilled in the art and could be made without departing from the scope of the information disclosed herein. All references cited are hereby incorporated by reference herein in their entireties and made part of this application.

What is claimed is:

1. A system for vaporizing a composition, the system comprises:
    at least one cartridge configured to house a composition, the at least one cartridge comprising a body, a valve, and a seal, wherein the at least one cartridge carries a bar code, quick response code, or near field communication tag;
    a scanner located at a positon suitable for scanning, the scanner configured to retrieve information from the bar code, quick response code, or near field communication tag on the at least one cartridge;
    an internal computing processor;
    a heating element operatively connected to the internal computing processor and configured to apply heat to the at least one cartridge;
    a mouthpiece with an opening and a vapor pathway for vapor to pass through from the at least one cartridge seal to the opening;

an air inlet operatively connected to the at least one cartridge;

an airflow sensor operatively connected to the air inlet and configured to measure air volume passing through the air inlet;

a user interface operatively connected to the internal computing processor and configured to display information;

an on-off electronic switch;

a battery;

a heating chamber wherein the at least one cartridge and the heating element are housed;

a battery chamber wherein the battery is housed; and a housing element to house the above components, wherein the internal computing processor is configured to collect and process information from the scanner, the on-off electronic switch, the airflow sensor, the heating element, and the user interface, to communicate with other computing processors outside of the system, and to control the system's operation, and wherein the heating element operates in heating cycles to control generated dosage, the heating cycle comprises:
  generating and transferring heat through the cartridge, its components, and content; and
  upon reaching a desired temperature and heat distribution, cooling the cartridge, its components, and content down before starting another heating cycle.

2. The system of claim 1, wherein the composition is a solid.

3. The system of claim 1, wherein the composition is a liquid.

4. The system of claim 1, wherein the information contained within the bar code, quick response code, or near field communication tag comprises ingredients of the composition, weight or volume of the composition, dosage, active ingredients and their quantity within the composition, and medical indications for the composition.

5. The system of claim 1, wherein the cartridge is designed to maximize internal surface area.

6. The system of claim 1, wherein the information collected from the internal computing processor comprises:
  individual session statistics for each use session concerning the heating element temperature, total vapor volume consumed, rate of puffing, time of day when the system is used, the time length of each session, quantity of composition used in each individual session, and symptom relief rating input by the user at the user interface;
  average statistics throughout the life of the system concerning average heating element temperature, average volume consumed, average rate of puffing during a use session, average time frequency of use per day, average quantity of composition used, and average symptom relief rating input by the user; and
  total statistics in the lifetime of the system concerning total number of vaporization sessions, total usage time, total cartridges used, total quantity of composition used, and total amount of gas volume consumed.

7. The system of claim 1, wherein the scanner is located on a wireless device.

8. The system of claim 1, wherein other computing processors that the internal computing processor communicates with are cloud-based processors, virtual machines, desktop computers, laptop computers, and mobile computers.

9. The system of claim 1, wherein other computing processors may be accessed and used through a user interface program.

10. The system of claim 9, wherein the user interface program is a mobile device application.

11. The system of claim 1, wherein the user interface is further configured to receive input information.

12. The system of claim 1, wherein the internal computing processor is configured to control the on-off electronic switch.

13. The system of claim 12, wherein the internal computing processor receives information from a remote computing processor and use the information to control the on-off electronic switch.

14. The system of claim 1, wherein the internal computing processor is further configured to locate and transmit information concerning the system's location.

15. The system of claim 1, further comprising a cooling system to cool the vapor existing the cartridge.

16. The system of claim 1, further comprising a LED indicator bar.

* * * * *